United States Patent [19]

Marshall et al.

[11] Patent Number: 5,658,277
[45] Date of Patent: Aug. 19, 1997

[54] APPARATUS FOR ELECTRICAL CONNECTION OF GLOVE MONITOR TO PATIENT

[75] Inventors: William H. Marshall; Robert E. Williams; John K. Bennett, all of Houston, Tex.

[73] Assignee: Novatec Medical Products, Inc., Houston, Tex.

[21] Appl. No.: 320,170

[22] Filed: Oct. 7, 1994

Related U.S. Application Data

[63] Continuation-in-part of Ser. No. 277,984, Jun. 22, 1994, Pat. No. 5,389,097, which is a continuation of Ser. No. 846,539, Mar. 4, 1992, abandoned, which is a continuation-in-part of Ser. No. 528,926, May 25, 1990, Pat. No. 5,114,425.

[51] Int. Cl.⁶ .................................................. A61B 17/36
[52] U.S. Cl. ................................................ 606/34; 340/540
[58] Field of Search ............................. 606/34; 128/641; 324/557; 340/540, 605; 174/55 G; 435/38–40, 909

[56] References Cited

U.S. PATENT DOCUMENTS

| | | |
|---|---|---|
| 1,772,232 | 8/1930 | Van Guilder . |
| 2,056,085 | 9/1936 | Alles ................................. 173/264 |
| 2,258,554 | 10/1941 | Heyer et al. . |
| 2,297,837 | 10/1942 | Loughnane . |
| 2,622,129 | 12/1952 | Killian . |
| 2,687,721 | 8/1954 | Ellison . |
| 2,874,695 | 2/1959 | Vaniman ............................ 128/138 |
| 2,981,886 | 4/1961 | Beck . |
| 3,093,793 | 6/1963 | Hicken . |
| 3,245,068 | 4/1966 | Wegryn et al. ..................... 340/235 |
| 3,414,808 | 12/1968 | Thomas . |
| 3,544,841 | 12/1970 | Peel . |
| 3,678,928 | 7/1972 | Mozes ................................ 128/138 |
| 3,759,246 | 9/1973 | Flack et al. ........................ 128/138 |
| 3,778,570 | 12/1973 | Shuman ............................. 200/61.05 |
| 3,832,993 | 9/1974 | Clipp ................................. 128/138 |
| 3,858,114 | 12/1974 | Voellmin et al. . |
| 3,980,073 | 9/1976 | Shaw, IV . |
| 3,980,077 | 9/1976 | Shaw, IV . |
| 4,069,817 | 1/1978 | Fenole et al. ...................... 128/138 |
| 4,094,320 | 6/1978 | Newton et al. . |
| 4,106,001 | 8/1978 | Mahoney ........................... 340/604 |
| 4,112,941 | 9/1978 | Lsarimore ......................... 128/641 |
| 4,122,854 | 10/1978 | Blackett . |
| 4,163,449 | 8/1979 | Regal ................................ 128/138 |
| 4,173,229 | 11/1979 | Halfon . |
| 4,178,589 | 12/1979 | Nunn et al. ........................ 340/573 |
| 4,184,486 | 1/1980 | Papa . |
| 4,191,950 | 3/1980 | Levin et al. ....................... 340/604 |
| 4,200,104 | 4/1980 | Harris . |
| 4,200,105 | 4/1980 | Gonser . |
| 4,206,632 | 6/1980 | Suzuki .............................. 73/40.5 |
| 4,212,295 | 7/1980 | Snyder .............................. 128/138 |
| 4,231,372 | 11/1980 | Newton . |
| 4,243,932 | 1/1981 | Kakumoto . |
| 4,244,371 | 1/1981 | Farin . |
| 4,245,649 | 1/1981 | Schmidt-Anderson . |

(List continued on next page.)

FOREIGN PATENT DOCUMENTS

| | | |
|---|---|---|
| 2.208.300 | 6/1974 | France . |
| 24 50 371 | 4/1975 | Germany . |
| 9310828 | 6/1993 | WIPO ................................ 606/34 |

OTHER PUBLICATIONS

"Device to Detect Glove Defects in Development", *Health Industry Today*, Jan. 1990.

*Primary Examiner*—Lee S. Cohen
*Attorney, Agent, or Firm*—Pravel, Hewitt, Kimball & Krieger

[57] ABSTRACT

Apparatus for electrically, detachably attaching a monitor such as a glove monitor between a health care worker and a patient utilizing a particular magnetic, electrical connection so that the health care worker can easily connect and disconnect from electrical connection to the patient for movement about the room or elsewhere.

10 Claims, 5 Drawing Sheets

U.S. PATENT DOCUMENTS

| | | | |
|---|---|---|---|
| 4,246,575 | 1/1981 | Purtell et al. | 340/605 |
| 4,273,531 | 6/1981 | Hasegawa . | |
| 4,303,073 | 12/1981 | Archibald . | |
| 4,321,925 | 3/1982 | Hoborn . | |
| 4,343,308 | 8/1982 | Gross . | |
| 4,365,637 | 12/1982 | Johnson . | |
| 4,459,993 | 7/1984 | Foreman . | |
| 4,494,541 | 1/1985 | Archibald . | |
| 4,525,814 | 7/1985 | Woodall . | |
| 4,539,559 | 9/1985 | Kelly et al. | 340/573 |
| 4,583,039 | 4/1986 | Kolcio . | |
| 4,653,491 | 3/1987 | Okada et al. | 128/138 |
| 4,687,004 | 8/1987 | Zenkich . | |
| 4,736,157 | 4/1988 | Betker . | |
| 4,738,260 | 4/1988 | Brown | 128/138 |
| 4,740,757 | 4/1988 | Converse . | |
| 4,751,467 | 6/1988 | Cooper . | |
| 4,754,264 | 6/1988 | Okada et al. | 340/573 |
| 4,754,757 | 7/1988 | Feucht . | |
| 4,760,383 | 7/1988 | DiLorenzo | 340/573 |
| 4,788,977 | 12/1988 | Farin . | |
| 4,810,971 | 3/1989 | Marable . | |
| 4,841,966 | 6/1989 | Hagen . | |
| 4,843,014 | 6/1989 | Cukier | 436/63 |
| 4,862,889 | 9/1989 | Feucht . | |
| 4,896,527 | 1/1990 | Akiba | 73/40.5 |
| 4,909,069 | 3/1990 | Albin et al. | 73/40 |
| 4,910,803 | 3/1990 | Cukier . | |
| 4,914,395 | 4/1990 | Hamada . | |
| 4,942,313 | 7/1990 | Helmit Kinzel . | |
| 4,942,364 | 7/1990 | Nishijima . | |
| 4,956,635 | 9/1990 | Langdon . | |
| 4,961,339 | 10/1990 | Kleis . | |
| 5,017,908 | 5/1991 | MacPherson | 340/605 |
| 5,036,309 | 7/1991 | Dennison, Jr. | 340/540 |
| 5,043,704 | 8/1991 | Blakeney | 340/573 |
| 5,109,215 | 4/1992 | Dennison . | |
| 5,204,632 | 4/1993 | Leach | 324/557 |
| 5,448,177 | 9/1995 | Thompson | 606/34 |

APPARATUS FOR ELECTRICAL CONNECTION OF GLOVE MONITOR TO PATIENT

SPECIFICATION

Cross-referenced to related applications.

This application is a continuation-in-part of U.S. patent application Ser. No. 08/277,984, now U.S. Pat. No. 5,389,097, entitled "Enhanced Monitoring Device for Surgical Gloves and Other Barriers" having a filing date of Jun. 22, 1994, which is a continuation of Ser. No. 07/846,539, filed Mar. 4, 1992, abandoned, which is a continuation-in-part of Ser. No. 07/528,926, filed May 25, 1990, U.S. Pat. No. 5,114,425.

FIELD OF THE INVENTION

The field of this invention relates to apparatus for the enhancement of electrical connection to patients of doctors, dentists and other health care workers in order to detect holes or other aberrations in barriers such as latex gloves.

BACKGROUND OF THE INVENTION

The adulteration of critical use articles such as surgical gloves and condoms poses considerable health risks. Adulteration as used herein is intended to encompass conditions such as holes formed during the manufacture of an article such as a surgical glove as well as holes formed thereafter for any reason, which holes may provide a path for adulteration of the article by potential dangerous fluids such as body fluids. The term "holes" or "perforations" include not only holes capable of initially passing fluid but also incipient holes, which may initially be too small to pass amounts of fluid but may enlarge over time, or otherwise breach or deteriorate the integrity of the barrier posed by the article. Such holes may even form a danger before reaching a size large enough to pass actual fluid since bacteria may theoretically pass through even smaller openings.

One example of a critical use article is the surgical glove. While problems with surgical gloves will be described shortly, it should be understood that similar problems may be present in any other type of barrier such as condoms, surgical gowns, surgical drapes and the like. The adulteration of gloves used in surgery has long been a problem to the medical doctor or other health care worker. There are two common sources for the creation of holes or perforations in surgical gloves prior and during use. One source is the manufacturer, who, due to lack of quality control or inherent manufacturing problems, may manufacture and sell gloves which already have perforations. In about 1990, the Federal Food and Drug Administration determined by field inspection failure rates of three to sixteen percent in surgical gloves prior to use. The FDA further found that, for patient-examination gloves, average defect rates ranged from 14–18%. In a recent attempt to tighten quality control in surgical gloves, the FDA resorted to its own modification of the well-known and fundamental A.S.T.M. technique for determining defects in gloves—a water fill test.

The second source of holes or perforations in gloves occurs during use. For example, holes or dangerously thin spots may develop in gloves at the time that the surgeon first fits the gloves over his or her hands, or, a glove may be perforated during surgery. Perforations during a surgery can occur because of penetration by sharp objects or because of the breaking down of inherently thin spots in the gloves or areas made thin as a result of putting the glove on the hand or manipulating instruments.

Perforations expose a surgeon to actual or possible contact with patient body fluids because of the resulting adulteration of the gloves. While such adulteration has always been a possible source of infection or the spreading of bacteria to the surgeon or from the surgeon to the patient, the alarming spread of hepatitis and AIDS viruses has created an even more serious problem—the possible spread of an incurable disease from the patient to the surgeon or from the surgeon to the patient. Therefore, the need for accurate and immediate detection of actual or near adulteration in surgical gloves is now at a heightened level because of the potential for the spread of incurable diseases from patient to surgeon or surgeon to patient.

The problems with the AIDS virus is not limited, however, to surgeons or other persons in the operating room such a nurses and anesthesiologists. For example, it is possible that other users of critical use gloves such as dentists or paramedics may be subject to many of the same serious concerns because the dentist or paramedic is also exposed to body fluids during his or her work on a patient. While perhaps less likely, there is also some possibility for the spread of serious diseases from patients to doctors during physical examinations. For purposes of definition, doctors, dentists, nurses and others who may be exposed to disease through gloves or other barriers are defined herein as "health care workers." It is also noted that the problem of communication of a disease between persons due to adulteration of a material acting as a barrier between the persons is not limited to surgical gloves but other articles such as surgical gowns, masks and condoms prevent similar problems.

While the FDA has taken the approach of using the rudimentary water fill method to determine leaks in gloves as manufactured, such simple techniques cannot be used to detect adulteration in gloves during use. There have been some attempts in the prior art to detect the occurrence of perforations in surgical gloves after the gloves are on the doctor's hands, all of which use resistance level detection as the parameter to detect holes. Such level detection concepts have been known for several decades and recently, there have been further attempts at modest improvement on such detection mechanisms, all of which continue to rely on resistance level detection as the principal parameter to be measured.

U.S. Pat. No. 4,321,925 of John Hoborn and Ulrich Krebbs discloses an electronic detector arranged so that the level of electronic conductivity through the gloves and between the patient and surgeon may be sensed at regularly recurring discrete time intervals in order to measure a predetermined level of sensed conductivity and signal an alarm if such predetermined level is met. The detecting circuit of the '925 patent is actually located in one of the shoes of the surgeon and includes one contact located in the insole of the shoe in order to make electrical contact with the surgeon and a second contact exposed to an electrical conducting plate located on the floor of the operating room so that a closed circuit is formed between the operating table, the patient, the doctor, the electrical device located in the shoe and the round conducting element or plate located on the floor of the operating room. The '925 patent teaches that five times per second the disclosed circuit short-circuits the contacts in the insole and in the bottom of the sole of the shoe in order to discharge static electricity from the insole contact which may have accumulated from the doctor. After each short circuit, the circuit is opened between the two contacts and a voltage level sensor is used to detect the level of electrical conductivity which occurs externally between the contacts.

The impedance of the latex or rubber that comprises surgical gloves is high. If there is a perforation in the operating gloves of the surgeon, which fills with body or other electrically conducting fluid, the impedance is thereby reduced and a greater conductivity is provided by the gloves. The '925 patent teaches that the occurrence of a perforation in the operating gloves may result in a relatively high electric conductivity between the surgeon and patient, thus allowing the sensing device to sound an alarm upon the occurrence of a predetermined level of sensed conductivity. Setting of the appropriate level of conductivity is strictly a matter of design and thus it is believed that one drawback to the device of the '925 patent is that the level of conductivity required to trigger the alarm may differ from glove to glove, depending upon the nature of the material, the thickness of the material and any other factors which may impact upon the general conductivity of the series circuit, which includes not only the doctor and patient, but also the doctor's shoes, a round plate located on the operating floor, and the operating table itself. Therefore, the '925 patent may work fairly well for certain types of gloves whose characteristics conform to the particular resistance level chosen for the resistance level sensor, but the '925 patent may not work well with many other types of gloves. In order to function properly, the resistance level sensor of the '925 patent would have to be adjusted to some pre-determined level depending upon the type of glove used and could even further require additional level adjustments during the period in which the glove is used.

Perhaps more importantly, the tendency of latex to absorb fluid during use is a factor not solved by the '925 Hoborn patent and other similar resistance level detection devices. Most natural rubber latex gloves absorb considerable quantities of water with time, referred to as hydration. This hydration effect causes the conductivity of the glove to increase markedly, thus decreasing its resistance. Eventually, the electrical resistance of the gloves becomes as low as a glove with a hole in it. Thus, for many types of surgeons, gloves, devices like that shown in the '925 patent will eventually give a hole alarm when there is no perforation. Therefore, the fact that the absolute conductivity of a glove varies with the hydration of the glove material detracts from the effectiveness of the sensor of the '925 device. There are other patents which disclose level detection type devices which are believed to have disadvantages similar to the '925 patent, such as U.S. Pat. Nos. 4,956,635 of Langdon and 5,036,309 of Dennison.

Other prior art devices include several devices that utilize a basin of conductive fluid in which the surgeon places his or her gloved hands for the purposes of determining whether or not the gloves have become adulterated. See U.S. Pat. Nos. 2,981,886 of Beck; 4,810,971 of Marable; 4,909,069 of Albin; and 4,956,635 of Langdon. If the conductive fluid in the basin enters a gloved hand or comes in contact with body fluid already in the adulterated glove, increased conductivity is detected. Other devices and relevant prior art will be discussed in appropriate submitted Information Disclosure Statements.

One solution to this problem is found in U.S. Pat. Nos. 5,144,425 of Robert E. Williams, William H. Marshall, Robert B. Stout and John J. McCourt, Jr., entitled "Method and Apparatus for Detecting Actual or Likely Adulteration of Critical Use Gloves." The '425 patent of Williams, et al. was issued on May 19, 1992 and discloses apparatus and method for detecting adulteration or a condition of near-adulteration of a glove in critical use application such as surgery where the gloves are worn by the surgeon and are exposed to the body fluids of a patient. The apparatus and method include a detection not only of a particular level of conductivity but also detection of a sudden change in conductivity which may be caused by a sudden change in condition of the glove, such as the opening of a hole in the glove or a sudden thinning of a glove. In this manner, the apparatus and method detect not only the actual condition of the glove but also a condition of change of the glove.

Following the same concept, but improving thereon, is U.S. patent application Ser. No. 07/846,539 the parent application to this application, entitled "Enhanced Monitor Device for Surgical Gloves and Other Barriers" filed on Mar. 4, 1992. In this patent application, an even newer and more improved monitoring device for detection of holes in gloves and other barriers is disclosed. The monitoring device can reliably monitor the integrity of gloves for an extended period and is suitable for use with a number of different glove-types from different glove manufacturers. The monitoring device is a programmable, configurable and self-adapting device which continuously measures the resistance, the rate of change or first derivative of resistance and the rate of the rate of change or second derivative of resistance across the gloves worn by the health care worker and a circuit comprised of the patient, health care worker and the gloves. The device distinguishes between sudden or rapid, transient change in resistance caused by a hole or puncture in the glove and a more gradual and/or continuous change in resistance caused by normal glove hydration. With the use of either the monitor of U.S. patent application Ser. No. 5,144,425 or the monitor of U.S. patent application Ser. No. 07/846,539, it is necessary that a convenient but highly reliable electrical connection be made between the doctor and patient so that the necessary electrical circuit can be completed upon the occurrence of a hole or other adulteration or aberration in the glove or other barrier. One such electrical connection is described with respect to the Hoborn '925 patent. However, such device requires the wearing of special shoes and the equipping of the operating room with a special conducting plate, which creates not only additional capital expense but also certainly additional maintenance expense.

It is desirable that an efficient, highly reliable but convenient electrical connection be made between the health care worker such as a doctor or dentist and the patient. Factors which cause this problem to be difficult to solve include the fact that the doctor, such as a surgeon during an operation, needs to be mobile. Therefore, the surgeon cannot be fixed to an operating table by some semi-permanent electrical connection which would prevent the surgeon from moving about the operating table or moving to another location to check an instrument, review x-rays or the like. Similarly, other health care workers such as dentists need to be able to move freely around a patient and within an office in order to organize equipment and be positioned properly for working on the patient.

SUMMARY OF THE INVENTION

It is an object of this invention to provide a system for electrical connection for health care workers which is easy to set up and attach and detach during actual use so that the health care worker such as a surgeon or dentist may be free to move about the patient or operating room as necessary.

Apparatus is provided for detachably, electrically connecting a monitor to detect holes or other anomalies in gloves or other barriers between a patient and health care worker. The apparatus includes a monitor for electrical attachment to a health care worker, the monitor being attached to the health care worker and including a first electrical conductor extending from the monitor to the health care worker. The monitor further includes a second, detachable electrical connection. The detachable electrical connection includes an electrical conductor having a first end connection electrically attached to the monitor and a second end terminating in a ferro-magnetic element in the form of a metallic disk, the magnetic element being electrically connectable to and detachable from an electrically conductive magnetic element. The electrically conductive magnetic element is attached to a patient's support member such as an operating table. The electrically conductive magnetic element includes an electrical connection extending between the electrical conductive magnetic element and a patient.

Utilizing this combination of elements, whenever the health care worker desires to electrically attach to the patient, the health care worker guides the monitor's second electrical conductor and the ferromagnetic end portion into electrical contact with the electrically conductive magnetic element attached to the patient support member. The electrically conductive element being magnetic, magnetically draws or pulls the ferro-magnetic element at the end of the second electrical connector into electrical connection when the ferro-magnetic element is positioned in proximity to the electrically conductive magnetic element. The electrical connection formed between the second electrical conductor extending from the monitor and the electrically conductive magnetic element is detachable so that the health care worker may move out of range of the second electrical conductor by merely pulling on the electrical conductor thereby detaching the magnetic connection between the ferro-magnetic element and the electrically conductive, magnetic element attached to the patient support member.

In another preferred embodiment of this invention, the monitor for determining holes or other anomalies in gloves may be mounted on a patient support member and include a first electrical conductor extending from the monitor to the patient and a second electrical conductor extending to an electrically conductive magnetic element also attached to the patient support member. The health care worker such as a dentist has a third conductor extending between attachment to the dentist and terminating a ferro-magnetic end portion which can be drawn into electrical connection with the electrically conductive magnetic element attached to the patient support member.

In another embodiment of this invention, the principle of the "slap bracelet" is adapted to be utilized as a quick connect and disconnect to a patient or other object so that immediate electrical contact may be made. In this embodiment, a thin piece of spring steel may be plated with silver and silver chloride and covered with a cloth impregnated with a conductive gel, such a sodium chloride. When the bracelet is in use, the tension in the spring steel maintains the required electrical contact.

The previous description has been merely a summary of the inventions described in this patent application and is not intended to describe the exact scope of patent protection.

DETAILED DESCRIPTION OF PREFERRED EMBODIMENT

Figure 1:
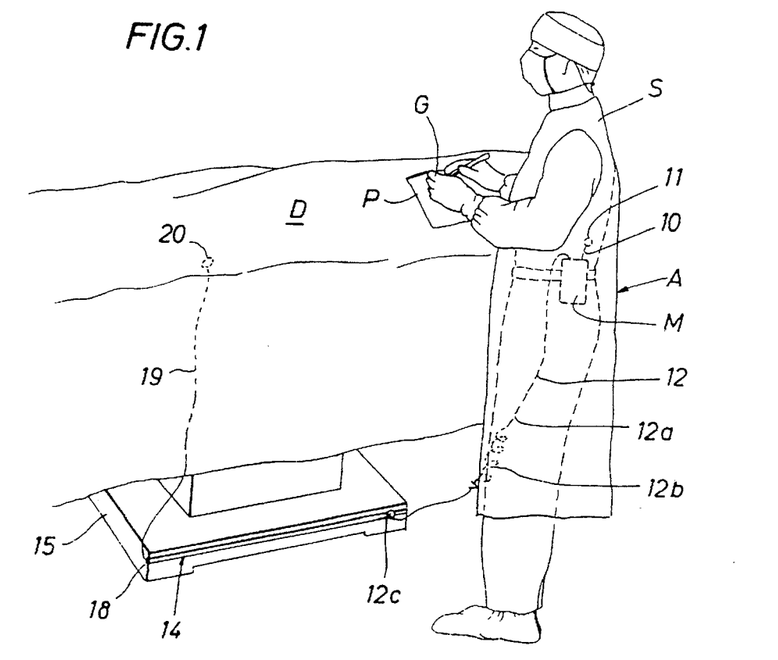
FIG. 1 is an overall view of the apparatus of this invention providing a detachable connection between a health care worker and patient.

Referring to the drawings and particularly FIG. 1, an apparatus A is provided for temporary attachment of a glove monitor M between the surgeon S and a patient P. It should be understood that while FIG. 1 illustrates a surgeon, that any other type of health care worker as previously defined may utilize the apparatus of this invention. The monitor M is a Glove Monitor of the type disclosed in U.S. Pat. No. 5,144,425, or as described in U.S. patent application Ser. No. 07/846,539, now co-pending, and which is a parent to this patent application. The apparatus A of this invention may also be utilized with other types of patient to health care worker monitors. As illustrated in FIG. 1 and other figures of the drawings, the glove monitor M is represented as a generally rectangular, small box or housing that includes the necessary hardware and software to detect electrical conductivity and changes therein across a barrier such as the gloves G worn by the surgeon S as illustrated in FIG. 1.

The glove monitor M includes a first electrical conductor 10 which terminates in any suitably known electrical connection, such as a EKG patch 11, which is adhered to the body of the surgeon S in order to establish electrical connection between the monitor M and the surgeon S.

Figure 2:
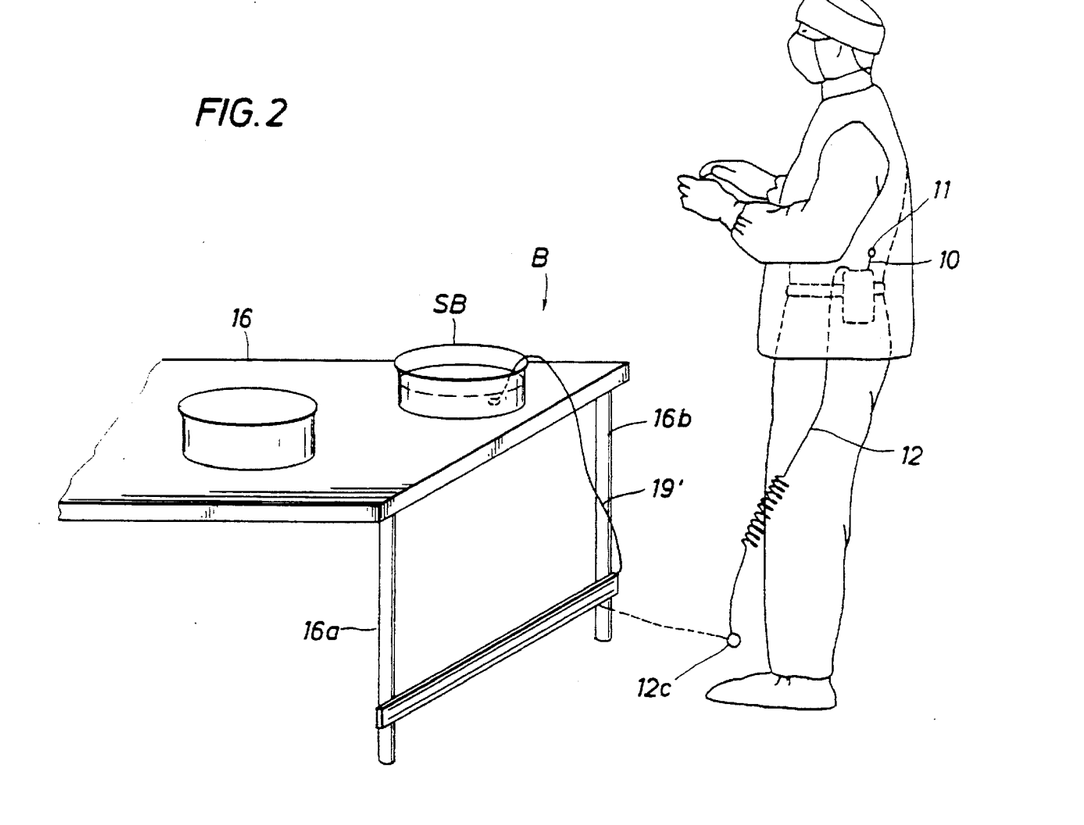
FIG. 2 is an overall view of the apparatus of this invention providing a detachable connection between the health care worker a sterile testing basin.

The monitor M includes a second electrical conductor 12 which extends between the monitor and an electrically conductive, magnetic element generally designated as 14 which is attached to the base 15 of an operating table (which is hidden from view by the patient drape D). The second electrical conductor 12 includes an electrical conductive wire lead which includes a first electrical connection between the monitor M and the wire lead such as through utilization of an input jack (not shown but well known in the art). The wire lead 12 includes a generally straight, flexible portion 12a and a coiled segment 12b to allow the surgeon S to move about the operating table without detaching the second lead 12 from electrical connection to the magnetic electrical connector 14. The electrical lead 12 terminates in a disk 12c made of a ferro-magnetic material. The disk 12c, as illustrated in FIGS. 1 and 2, is a circular disk of a thin ferromagnetic material which may easily be maneuvered by the surgeon into electrical connection with the magnetic electrical connector 14. The disc 12c may be made of other suitable material in which a magnetic field can be induced and which is electrically conductive.

Referring to FIG. 1, the magnetic electrical connector 14 is an electrically conductive magnetic strip which is attached to the base 15 of the operating table by any suitable means. The electrically conductive magnetic strip 14 may be a generally rectangular strip as illustrated in FIG. 1, approximately ⅛" in thickness and may contain a barium ferrite powder suspended in a rubber or plastic matrix in order to provide an attracting magnetic field. A suitable thin electrically conductive outer strip is attached to the magnetic strip such that the combination is both magnetic and electrically conductive. Such magnetic materials are well-known and readily available from companies such as Mag-Tech of Cincinnati, Ohio.

The combination of the ferro-magnetic disk 12c and the magnetic, electrical connector 14 provide a detachable electrical connection between the second electrical conductor 12 leading from the glove monitor M and the strip 14. The electrical circuit created is to be self closing when the ferro-magnetic disk is placed in close proximity to the magnetic strip 14. Further, the force required to disconnect the two members is important. If the holding force is too small, the connecting members will accidentally disconnect as the surgeon moves normally about during an operation. If the holding force is too great, the coiled wire section 12b of the second electrical conductor 12 can be extended to its limit before the members disengage. This may put an excessive pull force on the surgeon's pants and may also cause the ferro-magnetic disk to release with great velocity and possibly get entangled in other nearby wires, stands, medical tubing, and the like.

It has been found from practical experimentation in the operating room that a holding force should be preferably 9 plus or minus 7 ounces, and even more preferably 5 plus or minus 3 ounces. Therefore, the design of the magnetic member 14 and the ferro-magnetic disk 12c should be such as to fall within these parameters.

The ferro-magnetic disk should be very lightweight so that it will not swing around vigorously as the surgeon walks around the operating table or operating room. It has been found that a steel disk approximately two inches in diameter and having a thickness of 0.007" serves well. The mass of such disk is sufficiently low that it does not swing vigorously when unattached to the magnetic strip 14, but its diameter is sufficiently large that some part of the disk will be in close proximity to the magnetic strip 14 even if the disk is poorly located on the surgeon's pant leg. However, other sizes, shapes and thicknesses have been used and can be used successfully. In the preferred embodiment, the disk should weigh approximately 2.5 grams and preferably more than 0.5 grams.

In FIG. 1, a single magnetic strip 14 is illustrated. In the illustration of FIG. 1, a third electrical connection is made by a permanently mounted socket receiving a plug or a slideably attached disk 18 electrically attached to the magnetic strip 14 and having attached thereto a third electrical conductor 19 which extends from the magnetic disk or plug 18 into electrical connection with the patient through a suitable connector such as an EKG pad 20. Thus, in the electrical connection system of FIG. 1, whenever the electrical, conducting magnetic disk connector 12c is attached to the magnetic strip 14, an electrical circuit is completable between the monitor M, the surgeon, and the patient through the gloves G if there is a hole or another anomaly in the glove.

Referring to FIG. 2, the health care worker such as the surgeon S can test his or her gloves at any time using the test apparatus B. The test apparatus B includes the glove monitor M mounted with the health care worker S and including the first electrical conductor lead 10 and EKG patch 11 which electrically attach the monitor M to the health care worker. A second electrical lead 12 extends from the monitor M and terminates in the magnetic disc 12c. The magnetic strip 14 is mounted onto the legs 16a and 16b of a table or stand 16. A sterile basin SB containing saline solution is illustrated on the stand 16. The solution in the sterile basin is electrically attached to the magnetic strip 14 through electrical conductor 19', which electrically connects to the magnetic strip 14 and the conductive solution in the basin SB in any suitable manner. Preferably electrical contact with the conducting solution is made with a silver-silver chloride electrode attached to conductor 19'. The basin SB contains a sterile conductive fluid such as normal saline solution such that, if a hole should be present in the gloves G and fills with solution, an electrical circuit through the gloves will be completed utilizing the hardware and software of the monitor M as previously disclosed.

Figure 3:
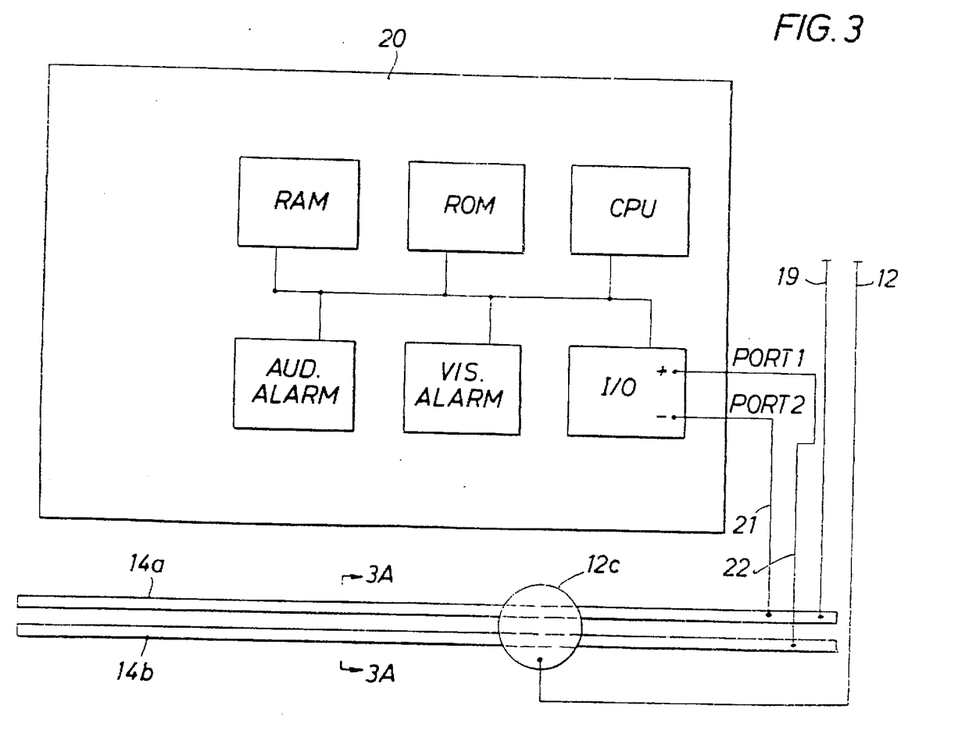
FIG. 3 is a schematic view illustrating an electronic alarm attachable to the electrically conductive magnetic element to sound an alarm in the event of electrical detachment by a ferro-magnetic member which is electrically connected to the monitor and health care worker.

Referring to FIG. 3, two magnetic, electrical conducting strips 14a and 14b are utilized in conjunction with an alarm circuit generally designated as 20. The alarm circuit 20 is electrically connected to both magnetic, electrically conducting strips 14a and 14b through leads 21 and 22. In the embodiment of FIG. 3, the third electrical conductor 19 extends from electrical connection to one of the magnetic strips 14a into electrical connection with the patient P as illustrated in FIG. 1. The electrical connection of leads 21–22 and of conductor 19 is only shown schematically. It is contemplated that each lead 21–22 and 19 will terminate in a plug which is insertable into a socket in electrical connection with the strips 14a and 14b as shown in FIG. 3.

Figure 3A:
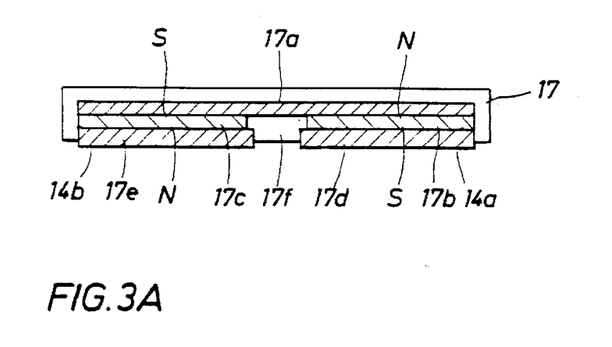
FIG. 3A is a side view in section taken along line 3A—3A of FIG. 2 of the composite magnetic, electrically conducting strips which provide the detachable connection between the health care worker and the patient.

The magnetic strips 14a–14b are actually composites strips made up of several layers of strip-like material having different characteristics. Referring to FIG. 3A, first of all, the strip composites 14a and 14b are mounted within a generally U-shaped plastic frame 17. A ferro-magnetic strip generally designated as 17a is mounted within the U-shaped plastic frame 17 and provides the inner-most layer. A first strip 17b of flexible magnetic material is mounted onto the layer 17a in the upper portion of the recess formed by the U-shaped frame 17. A second, lower magnetic strip 17c is mounted in the lower portion of the recess such that the two strips 17b and 17c extend horizontally (FIG. 3) with a space between them. The flexible magnetic material for the strip 17b and 17c is the same as the material described with respect to the magnetic strip 14 in that the strip contains a barium ferrite powder suspended in a rubber or plastic matrix in order to provide an attracting magnetic field. The strip 17b, and thus the composite strip 14a, is magnetized as illustrated in FIG. 3A while the strip 17c, and thus the composite strip 14b, has opposite poles as also illustrated in FIG. 3A. Finally, a strip of ferro-magnetic, conducting material, such as steel, and designated as 17d is attached to the outer most surface of the magnetic strip 17b. Similarly, a ferro-magnetic, steel strip 17e is attached to the outside surface of the magnetic strip 17c. Each of the strips 17d and 17e, which form the final layer of the composite strips 14a and 14b, respectively, extend slightly beyond the outside flanges of the U-shaped frame member 17 so that the disc 12c will be placed directly in contact with the composite strips 14a and 14b when the disc 12c is moved sufficiently close to the composite strips 14a and 14b. A horizontally extending plastic spacer 17f, which is T-shaped in the cross-section of FIG. 3, extends the length of the composite strips 14a and 14b to maintain stability and separation between the composite strips.

The alarm circuit 20 of FIG. 3 includes a Motorola 68 HC11 microprocessor, which includes RAM and ROM memories and a central processing unit CPU. The Aud. (audible) ALARM is a piezoelectric oscillator (such as International Components Corp. BRT 1209P). The visible alarm is a high efficiency light emitting diode (such as the Hewlett Packard HLMP 1700).

Figure 5:
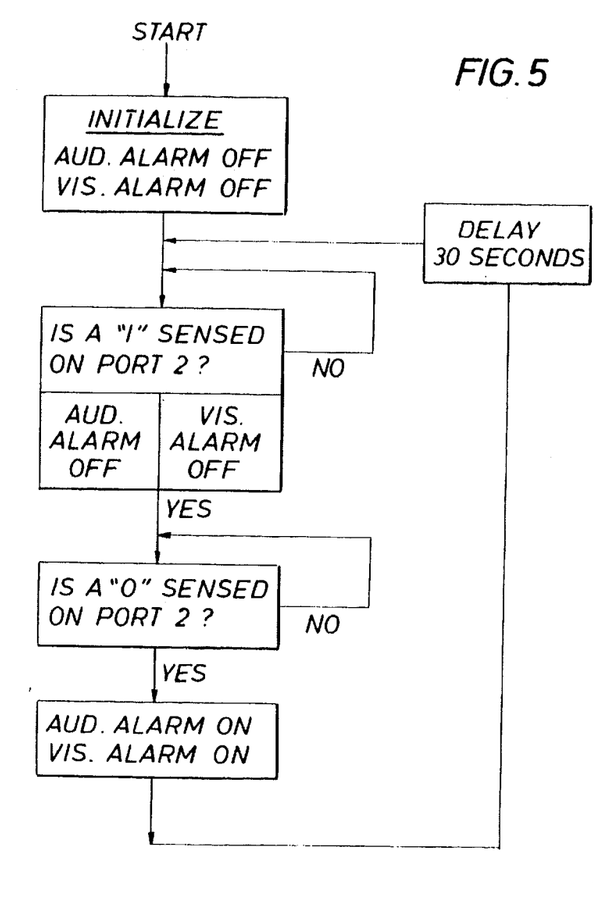
FIG. 5 is a schematic flow chart of the software for each of the alarms circuits of FIGS. 3 and 4.

The CPU outputs current on the positive (+) Port 1 (line 22 in FIG. 3) and senses for a "1" or "0" on the negative port (Port 2) (line 21 in FIG. 2). If disc 12c is in contact with both electrical conducting magnetic strips 14a and 14b, then a "1" will be sensed. If the disc 12c is not in electrcal contact with both electrically conductive magnetic strips 14a and 14b, then "0" will be sensed and the alarms will be activated. Referring to FIG. 5, the software is essentially the same for both alarms 20 and 30.

Figure 4:
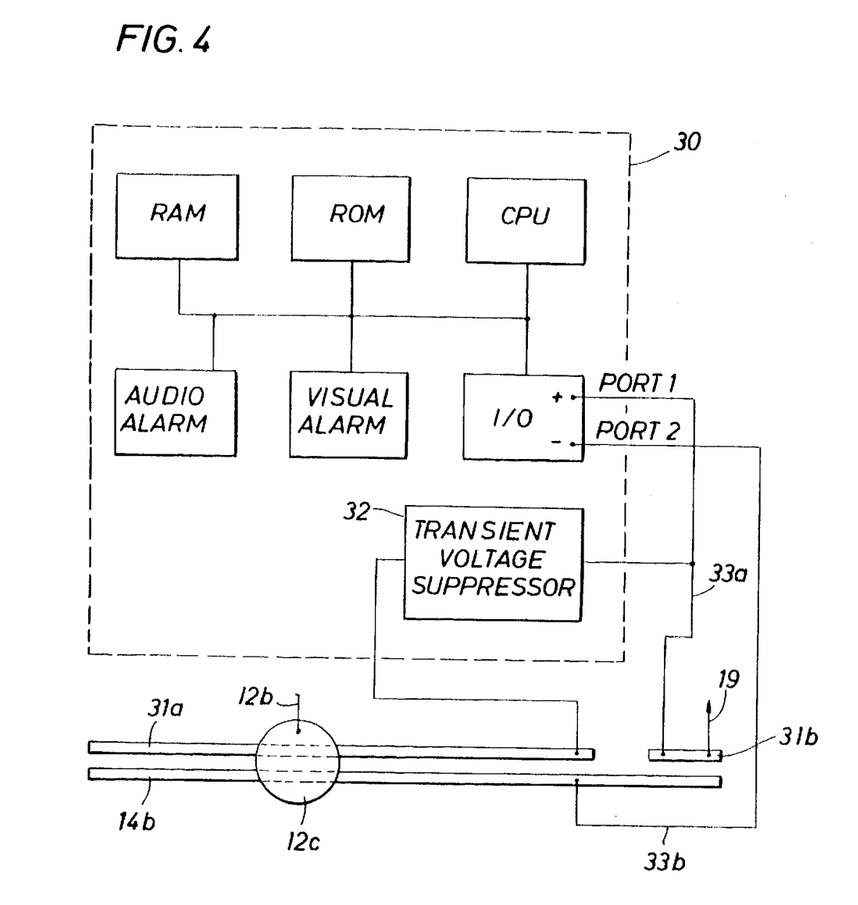
FIG. 4 is a schematic view of a second embodiment of the electronic alarm containing an additional feature to prevent dangerous feedback voltage.

FIG. 4 illustrates another embodiment 30 which includes RAM and ROM memories and a central processing unit with AUDIO and VISUAL ALARMS, previously described with respect to alarm 20. Additionally, a surge protector known as a transient voltage suppressor (such as the supressor made by Diodes, Inc. 1.5KE12CA) is utilized. The magnetic strip connector of FIG. 4 again includes a bottom magnetic, electrically conducting strip 14b; but, the upper strip is actually two strip portions 31a and 31b, which are interconnected by the transient voltage suppressor 32. The transient voltage suppressor 32 is electrically connected into lead 33a, which extends into port 1 of the alarm 30. Port 2 of the alarm 30 is electrcally connected by lead 33b to the bottom magnetic, electrical conductor 14b. The lead 19 extends from the magnetic strip portion 31b to the patient P. Should there be any surge voltage such as from use of a defibrillator, the suppressor will be electrically open circuited to prevent any dangerous feedback voltage being conducted to the health care worker if the health care worker forgets to disconnect himself or herself from the connector during defibrillation. As an example, the suppressor may be set to open at 11 volts or greater.

Figure 6:
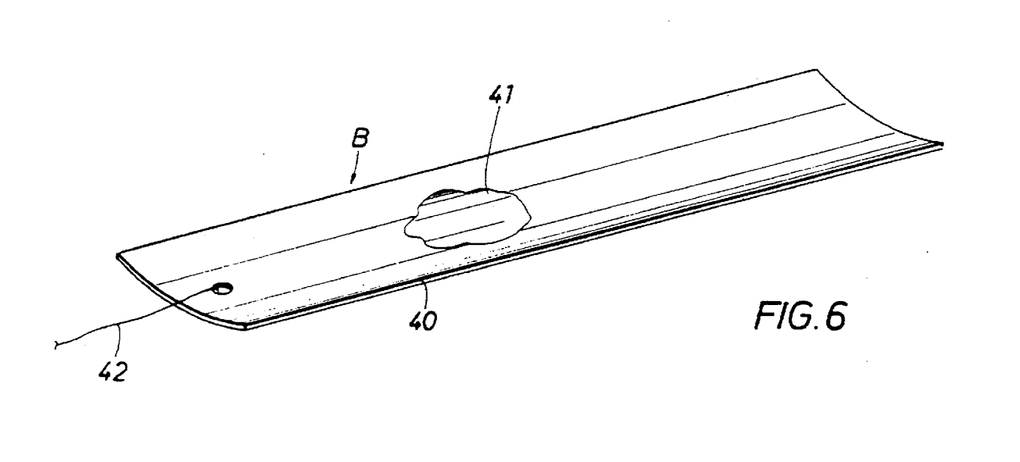
FIG. 6 is a perspective view of the coilable electric connector which may be utilized in this invention.
Figure 7:
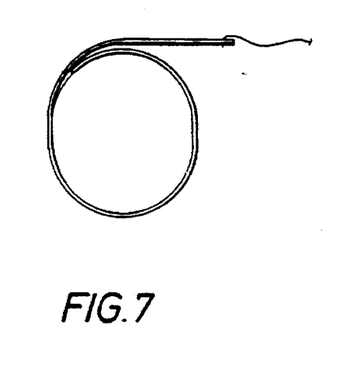
FIG. 7 is a side view illustrating the coilable electrical connector in the coiled position in electrical connection to the appendage of a patient.
Figure 8:
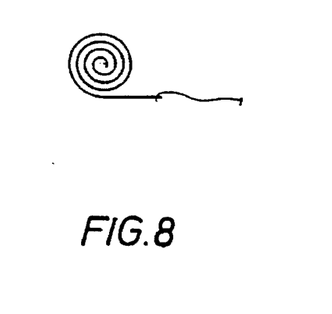
FIG. 8 is a side view of the coilable electrical connector in a fully coiled position of non-use.

FIGS. 6-8

Referring to FIGS. 6-8, another apparatus B is provided for making a quick electrical attachment and detachment. The apparatus B is a substantially thin, resilient, generally rectangular metallic member 40 which is capable of coiling upon itself in the manner illustrated in FIG. 8 or upon an arm, leg, or other appendage of a patient such as illustrated in FIG. 4. The coilable electrical connector 40 of FIGS. 6-8 takes the principle of the toy known as a "slap bracelet" and applies it to forming a detachable electrical connector. The member 40 may be a stainless spring steel plated with silver and silver chloride on one side and covered with a porous cloth 41 which may be saturated or moistened with a sodium chloride solution or other similar chloride-containing conductive gel. The electrical connector 40 is attached to a wire 42 which may be the same wire as wire 12 leading to the monitor M, as illustrated in FIG. 1, or another wire which extends into electrical connection with the monitor M attached to any health care worker.

Taking the principle of the toy known as the "slap bracelet," the coilable member 40 may be easily applied to an arm or leg by gently "slapping" the coilable element against the arm or leg. The resilient strength of the spring steel maintains the coiled physical connection, such as illustrated in FIG. 7, so that an electrical connection is made through the conductive gel. There may be other uses, such as non-sterile usage, where it is desirable to utilize the inherent coilability of the quick connector 40 which allows for easy storage. For example, in non-sterile usage, the coilable electrical connector 40 may be kept in the pocket of the coat of a health care worker and pulled out and quickly wrapped around an object such as the patient's arm or leg in order to make a non-sterile electrical connection. The uses of such a connection extend not only to the medical community but also to other areas where it may be desirable to make a quick electrical connection and electrical disconnection around an object about which a coilable electrical conductor 40 may be mounted. Within the medical environment, the electrical connector of this invention may be utilized with other suitable electrical equipment.

Figure 9:
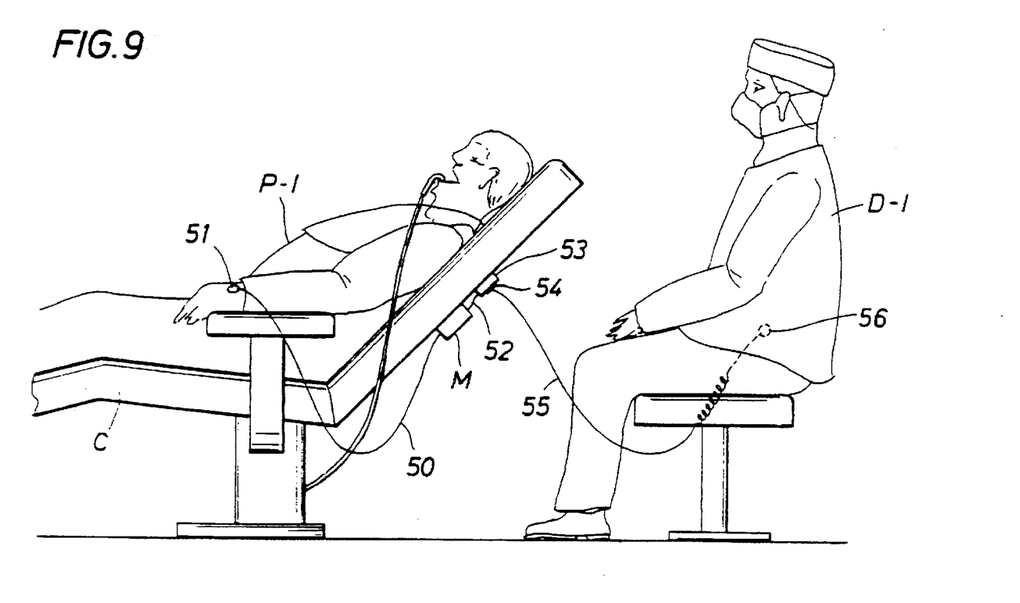
FIG. 9 is a side view of another preferred embodiment of this invention illustrating the detachable electrical connection between a health care worker such as a dentist and patient.
Figure 10:
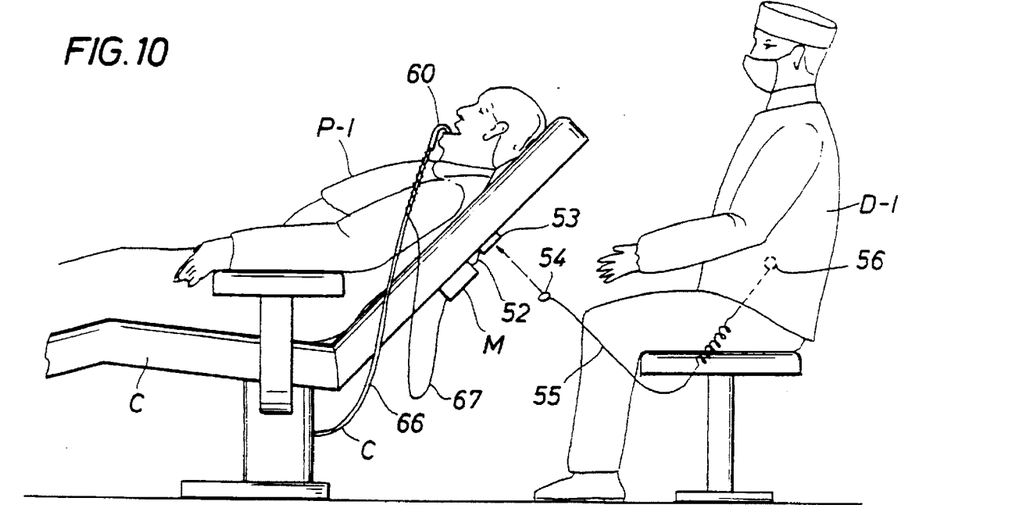
FIG. 10 is a an alternate, preferred embodiment to the embodiment of FIG. 6 for electrical connection of a health care worker such as a dentist to a patient.
Figure 11:
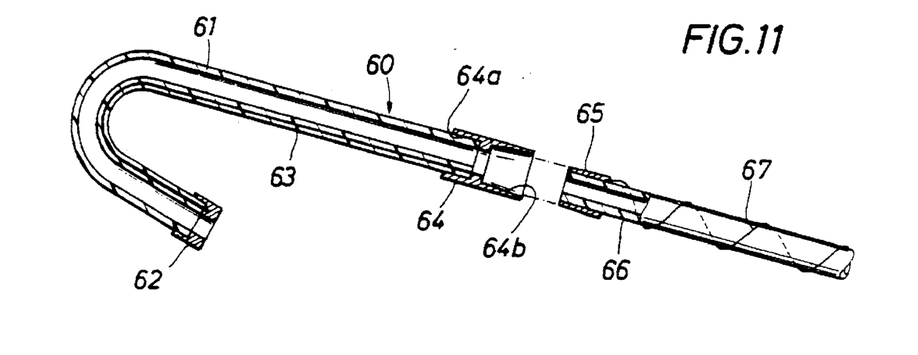
FIG. 11 is a side view and section illustrating a disposable saliva ejector which is also capable of providing an electrical connection to the patient of a dentist.

FIGS. 9-11

Referring now to FIG. 9, an apparatus is provided for electrical connection of a glove monitor between a sitting health care worker such as a dentist D-1 and a patient P-1. In the embodiment of FIG. 9, the glove monitor M is attached by any suitable means to the back of a dental chair C. The glove monitor M includes the first conductor or lead 50 which extends from electrical connection to the glove monitor M to electrical connection through an EKG patch 51 to the patient P-1. The glove monitor includes a second electrical conductor 52 which extends to an electrically conductive, magnetic strip 53 attached to the back of the dental chair. The magnetic strip 53 is similar to the magnetic strips 14, 14a and 14b except for size and provides a magnetic field to attract a ferro-magnetic disk 54, which is attached at the end of electrical conductor 55 which extends into electrical connection by means of EKG patch 56 with the dentist D-1. In this manner, the dentist D-1 can easily electrically connect and disconnect to the magnetic electrical connector 53 so that the dentist may move about the room as necessary to perform tasks. The magnetic strength of the electrically conductive, magnetic element 53 is similar to that described for magnetic conductors 14, 14a and 14b so that the dentist D-1 can easily detach from electrical connection by simply pulling away from the chair and thereafter easily reconnect. The embodiment of FIG. 9 is also applicable to the embodiment of FIG. 1 for the operating room environment so that the monitor M would be located on the operating table base rather than on the surgeon S.

Referring now to FIGS. 10 and 11, another embodiment for use of the glove monitor M with a patient P-1 is illustrated. In the embodiments of FIGS. 10 and 11, the glove monitor M is again attached to the back of the dental chair C. The electrical lead 52 terminates in electrical connection to the magnetic electrical connector 53, which detachably receives the ferromagnetic disk 54, which is attached to lead 55 which terminates in EKG patch 56 in electrical connection with the dentist D-1. However, instead of a direct electrical lead from the monitor M to the patient P-1 as illustrated in FIG. 9, the electrical connection from the monitor M to the patient P-1 is made utilizing a disposable saliva ejector 60, as illustrated in detail in FIG. 11.

The disposable saliva ejector includes the generally U-shaped saliva tube 61 of the type that is in well known use today. However, the first end of the saliva tube terminates in an electrically conductive ring 62 which contacts the inside of the mouth of the patient. A conductive wire 63 extends into electrical attachment with ring 62 and an electrical, tubular coupling 64. The electrical coupling 64 is a generally tubular electrical conductor which includes a first circular recess 64a to receive the conductor 63 and the saliva tube 61. The other end of the conductor 64 includes a tapered, circular recess 64b adapted to receive a male, annular conductor 65 which is mounted at the end of the vacuum hose 66 which extends to the vacuum connection located on the dentist chair C or elsewhere. A conductor 67 is electrically attached to the male connector 65 and is wrapped around a portion of the vacuum supply tube 66 and extends into electrical connection with the glove monitor M. In this manner, an electrical connection is made automatically by using the disposable, electrically conductive saliva ejector, and thus it is unnecessary to actually attach a separate line 51 to the patient as used in FIG. 9. The saliva ejector 61 may be manufactured of disposable materials so that a new, sterile ejector may be available for each patient.

The various embodiments described herein are usable to provide a temporary, detachable electrical connection between the glove monitor M and patients, whether located in dental chairs or on operating tables, or elsewhere. It is within the scope of this invention to utilize the principles of this invention with various types of health care workers as well as patients located in almost any environment.

Having described the invention above, various modifications of the techniques, procedures, material and equipment will be apparent to those in the art. It is intended that all such variations within the scope and spirit of the appended claims be embraced thereby.

What is claimed is:

1. Apparatus for detachably, electrically connecting a glove monitor to a patient in order to detect holes or other anomalies in gloves during use, comprising:

a glove monitor adapted for electrical attachment to a health care worker, said glove monitor including means adapted for attachment to said health care worker and including a first electrical connection adapted to extend from said glove monitor to said health care worker;

an electrically conductive, magnetic element and means for attachment of said electrically conductive magnetic element to a patient support member, said electrically conductive, magnetic element including a second electrical connection, said second electrical connection adapted to extend between said electrically conductive, magnetic element and a patient;

said glove monitor having a detachable electrical lead extending therefrom, said detachable electrical lead including an electrical conductor having a first end for connection to said glove monitor and a second end terminating in a detachable ferro-magnetic element, said detachable ferromagnetic element being electrically connectable to and detachable from said electrically conductive, magnetic element attached to said patient support member whereby a health care worker is able to electrically connect said glove monitor to said patient and electrically detach said glove monitor from said patient as necessary.

2. Apparatus of claim 1, further including:

said electrically conductive, magnetic element being a generally elongated strip of magnetic material including an electrically conductive portion for attachment to said patient support member; and, said second electrical connection including a second electrical conductor having a first end electrically attached to said magnetic strip and a second end terminating in an electrically conductive element adapted for attachment to said patient.

3. Apparatus of claim 1, further including:

said electrically conductive magnetic element being formed of at least two generally elongated strips of magnetic material having electrically conductive portions for attachment to said patient support member, said elongated strips being attachable in adjacent, parallel relationship; and said second electrical connection including a second electrical conductor having a first end electrically attached to said electrically conductive portions of the at least two generally elongated strips of magnetic material and a second end terminating in an electrically conductive element adapted for attachment to said patient.

4. Apparatus of claim 3, including:

said detachable ferro-magnetic element being of sufficient size to electrically attach to both of said electrically conductive portions of said magnetic strips simultaneously.

5. Apparatus of claim 1, including:

said electrically conductive magnetic element having a magnetic attraction, said magnetic attraction of said electrically conductive, magnetic element being sufficiently strong to draw said detachable ferro-magnetic element into electrical connection whenever said detachable ferromagnetic element is in close proximity to said electrically conductive magnetic element.

6. Apparatus of claim 1, including:

said electrical conductor of said detachable electrical lead having a coiled portion such that said attachment of said second end detachable ferro-magnetic element to said electrically conductive, magnetic element attached to said patient support member is yieldable to allow said health care worker freedom of movement while maintaining electrical connection between said detachable ferro-magnetic element and said magnetic element.

7. Apparatus of claim 1, including:

an alarm circuit in electronic communication with said electrically conductive magnetic element and including alarm means to sound an alarm whenever said detachable ferro-magnetic element is separated from attachment to said electrically conductive magnetic element.

8. Apparatus of claim 7, wherein:

said alarm means includes signal means indicating whenever said detachable ferromagnetic element is detached from said electrically conductive magnetic element.

9. Apparatus of claim 8, including:

said alarm means including means for suppressing any undesirable voltage surge from said lead extending to said patient.

10. Apparatus for detachably, electrically connecting a glove monitor to a patient supported on a patient support structure in order to detect holes or other anomalies in gloves during use, comprising:

a glove monitor;

said glove monitor including an electrical circuit which is adapted to extend in one direction between the patient and the health care worker, said electrical circuit including a detachable electrical connection, said detachable electrical connection including an electrical lead including a conductor which terminates in a detachable ferro-magnetic element, and a stationary, electrically conductive magnetic element adapted to be mounted on said patient support structure, said detachable ferro-magnetic element being electrically connectable and detachable from said stationary electrically conductive magnetic element whereby electrical connection between said health care worker and said patient is detachable and reattachable when said ferro-magnetic element is placed in close proximity to said electrically conductive stationary magnetic element.

* * * * *